United States Patent [19]

Dubief et al.

[11] Patent Number: 5,700,456
[45] Date of Patent: Dec. 23, 1997

[54] COMPOSITIONS FOR THE TREATMENT AND PROTECTION OF HAIR, BASED ON CERAMIDE AND/OR GLYCOCERAMIDE AND ON POLYMERS CONTAINING CATIONIC GROUPS

[75] Inventors: Claude Dubief, Le Chesnay; Daniele Cauwet, Paris, both of France

[73] Assignee: L'Oreal, Paris, France

[21] Appl. No.: 426,799

[22] Filed: Apr. 24, 1995

[30] Foreign Application Priority Data

Apr. 21, 1994 [FR] France ............... 94 04881

[51] Int. Cl.⁶ ................. A61K 7/06; A61K 7/48
[52] U.S. Cl. ................. 424/70.17; 424/70.11; 424/70.27; 424/70.28; 424/401
[58] Field of Search .............. 424/401, 70.1, 424/70.13, 70.14, 70.17, 70.27, 70.28; 514/781; 554/61, 63, 68, 108, 109, 110

[56] References Cited

U.S. PATENT DOCUMENTS

| | | |
|---|---|---|
| 2,261,002 | 10/1941 | Ritter. |
| 2,271,378 | 1/1942 | Searle. |
| 2,273,780 | 2/1942 | Dittmar. |
| 2,375,853 | 5/1945 | Kirby et al.. |
| 2,388,614 | 11/1945 | Kirby et al.. |
| 2,454,547 | 11/1948 | Bock et al.. |
| 2,961,347 | 11/1960 | Floyd. |
| 3,206,462 | 9/1965 | McCarty. |
| 3,227,615 | 1/1966 | Korden. |
| 3,874,870 | 4/1975 | Green et al.. |
| 3,929,990 | 12/1975 | Green et al.. |
| 3,966,904 | 6/1976 | Green et al.. |
| 4,001,432 | 1/1977 | Green et al.. |
| 4,005,193 | 1/1977 | Green et al.. |
| 4,025,617 | 5/1977 | Green et al.. |
| 4,025,627 | 5/1977 | Green et al.. |
| 4,025,653 | 5/1977 | Green et al.. |
| 4,026,945 | 5/1977 | Green et al.. |
| 4,027,020 | 5/1977 | Green et al.. |
| 4,839,166 | 6/1989 | Grollier et al. ........ 424/70.13 |
| 5,096,455 | 3/1992 | Grollier ........ 8/410 |
| 5,439,673 | 8/1995 | Murray ........ 424/70.12 |

FOREIGN PATENT DOCUMENTS

| | | |
|---|---|---|
| 0 122 324 | 10/1984 | European Pat. Off.. |
| 122 324 | 10/1984 | European Pat. Off.. |
| 0 278 505 | 8/1988 | European Pat. Off.. |
| 0278505 | 8/1988 | European Pat. Off.. |
| 278 505 | 8/1988 | European Pat. Off.. |
| 0 474 023 | 3/1992 | European Pat. Off.. |
| 474 023 | 3/1992 | European Pat. Off.. |
| 0 495 624 | 7/1992 | European Pat. Off.. |
| 495 624 | 7/1992 | European Pat. Off.. |
| 1 583 363 | 10/1969 | France. |
| 2 162 025 | 7/1973 | France. |
| 2 252 840 | 6/1975 | France. |
| 2 270 846 | 1/1976 | France. |
| 2 280 361 | 2/1976 | France. |
| 2 316 271 | 1/1977 | France. |
| 2 320 330 | 3/1977 | France. |
| 2 333 012 | 6/1977 | France. |
| 2 336 434 | 7/1977 | France. |
| 2 368 508 | 5/1978 | France. |
| 2413907 | 8/1979 | France. |
| 2 679 770 | 2/1993 | France. |
| 2679770 | 2/1993 | France. |
| WO 92/06982 | 4/1992 | WIPO. |
| 93/02656 | 2/1993 | WIPO. |
| WO 93/02656 | 2/1993 | WIPO. |
| WO 94/03151 | 2/1994 | WIPO. |

*Primary Examiner*—Melvyn I. Marquis
*Assistant Examiner*—Robert H. Harrison
*Attorney, Agent, or Firm*—Finnegan, Henderson, Farabow, Garrett & Dunner, L.L.P.

[57] ABSTRACT

Composition for the treatment and protection of hair, containing, in a cosmetically acceptable medium, at least one ceramide and/or glycoceramide and at least one cationic polymer containing primary, secondary or tertiary amine groups or quaternary ammonium groups in the chain and having a viscosity at a concentration of 1% by weight of active substance in water of less than 15 mPa.s, the composition containing less than 4% by weight of anionic and/or amphoteric and/or zwitterionic surfactants.

18 Claims, No Drawings

COMPOSITIONS FOR THE TREATMENT AND PROTECTION OF HAIR, BASED ON CERAMIDE AND/OR GLYCOCERAMIDE AND ON POLYMERS CONTAINING CATIONIC GROUPS

The present invention relates to compositions intended for the treatment and protection of hair and containing, in a cosmetically acceptable medium, at least one ceramide and/or glycoceramide and one cationic polymer containing nitrogen atoms in the main chain.

The invention also relates to the cosmetic treatment process employing such compositions.

Hair-care formulations which make it possible to treat hair which has been damaged by inclement weather or by unsuitable hair treatments are already known in the prior art. Cationic polymers which have the advantage of improving these cosmetic properties, inter alia, the disentangling and the softness of wet and dried hair, and also of protecting the hair fibers from these harmful agents, have already been used for this purpose. However, some cationic polymers have unsatisfactory disentangling properties, and have a tendency, for example, when treatments are superposed, to make the hair lank and feel coarse.

Ceramides or glycoceramides which have already been combined with cholesterol esters for the purpose of protecting the hair fibre are also known. Application of these latter compositions or of ceramides alone to the hair result, however, in cosmetic performance parameters which are inadequate, both on wet hair and on dried hair. The inventors have discovered that, surprisingly, the combination of ceramides or glycoceramides with certain cationic polymers results in especially advantageous cosmetic properties, in particular as regards wet disentangling. In particular, the inventors found that the combination had a synergistic effect which is not simply the addition of the properties of the two components, in particular in non-detergent media having a low or zero concentration of washing surfactants.

The inventors found that this effect was more especially obtained by combining ceramides or glycoceramides with cationic polymers containing primary, secondary or tertiary amine groups or quaternary ammonium groups in the main chain and having a viscosity at a concentration of 1% by weight in water of less than 15 mPa.s.

In PCT Application WO 93/02656, the use was envisaged of cationic dispersions of ceramides or glycoceramides; the cationic surfactants used in such dispersions are, however, different from the cationic polymers employed according, to the invention, and do not enable the desired effects to be obtained, inter alia they do not enable the fibers to be protected.

The present invention is therefore drawn to a non-washing composition intended for the treatment and protection of hair, based on ceramide and/or glycoceramide and on cationic polymers.

The present invention is also drawn to a process for the cosmetic treatment of hair, employing such a composition.

Other subjects of the invention will become apparent on reading the description and the examples which follow.

The composition intended for the treatment and protection of hair according to the invention is essentially characterized in that it contains, in a cosmetically acceptable medium, at least one ceramide and/or glycoceramide and at least one cationic polymer containing nitrogen atoms in the main chain and whose viscosity at a concentration of 1% in water is less than or equal to 15 mPa.s, the composition containing less than 4% of anionic and/or amphoteric and/or zwitterionic surfactants.

The cationic polymers which are usable according to the invention are chosen from cationic polymers containing primary, secondary, tertiary or quaternary amine groups in the main polymer chain. They have a molecular weight greater than 500, and preferably greater than 1,000. These polymers display, moreover, the viscosity properties defined above.

The cationic polymers which are preferably usable according to the invention are chosen from:

(1) Polymers comprising piperazinyl units and bivalent alkylene or hydroxyalkylene radicals having unbranched or branched chains optionally interrupted by oxygen, sulphur or nitrogen atoms or by aromatic or heterocyclic rings, as well as the oxidation and/or quaternization products of these polymers. Such polymers are described in French Patents FR 2,162,025 and FR 2,280,361, the disclosures of which are hereby incorporated by reference.

(2) Water-soluble polyaminoamides prepared, in particular, by polycondensation of an acidic compound with a polyamine. These polyaminoamides may be cross-linked with an epihalohydrin, a diepoxide, a dianhydride, and unsaturated anhydride, a bis-unsaturated derivative, a bis (halohydrin), a bis (azetidinium) compound, a bis (haloacyl) diamine or a bis(alkyl halide), or alternatively with an oligomer resulting from the reaction of a bifunctional compound which is reactive towards a bis(halohydrin), a bis (azetidinium) compound, a bis (haloacyl) diamine, a bis (alkyl halide), an epihalohydrin, a diepoxide or a bis-unsaturated derivative; the crosslinking agent being used in proportions ranging from 0.025 to 0.35 mol per amine group of the polyaminoamide.

These polyaminopolyamides may be alkylated or, if they contain one or more tertiary amine functions, quaternized. Such polymers are described, in particular, in French Patents FR 2,252,840 and FR 2,368,508, the disclosures of which are hereby incorporated by reference.

(3) Polyaminoamide derivatives resulting from the condensation of polyalkylenepolyamines with polycarboxylic acids, followed by an alkylation with bifunctional agents.

There may be mentioned, for example, adipic acid/dialkylaminohydroxyalkyl/dialkylenetriamine polymers in which the alkyl radical contains from 1 to 4 carbon atoms and preferably denotes methyl, ethyl or propyl. Such polymers are described in French Patent FR 1,583,363, the disclosure of which is hereby incorporated by reference. Among these derivatives, the adipic acid/dimethylaminohydroxypropyl/diethylenetriamine polymers sold under the name "CARTARETINE F, $F_4$ or $F_8$" by the company SANDOZ may be mentioned more especially.

(4) Polymers obtained by reacting a polyalkylenepolyamine containing two primary amine groups and at least one secondary amine group with a dicarboxylic acid chosen from diglycolic acid and saturated aliphatic dicarboxylic acids having from 3 to 8 carbon atoms; the mole ratio of the polyalkylenepolyamine to the dicarboxylic acid being from 0.8: 1 to 1.4: 1; the polyaminoamide resulting therefrom being reacted with epichlorohydrin in a mole ratio of epichlorohydrin to the secondary amine group of the polyaminoamide of from 0.5: 1 to 1.8: 1. Such polymers are described especially in U.S. Pat. Nos. 3,227,615 and 2,961,347, the disclosures of which are hereby incorporated by reference.

Polymers of this type are marketed, in particular, under the name "HERCOSETT 57" by the company HERCULES INCORPORATED or alternatively under the name "PD 170" or "DELSETTE 101" by the company HERCULES in the case of the adipic acid/epoxypropyl/diethylenetriamine copolymer.

(5) Methyldiallylamine or dimethyldiallylammonium cyclohomopolymers, such as the homopolymers containing as main constituent of the chain units corresponding to the formula (I) or (II):

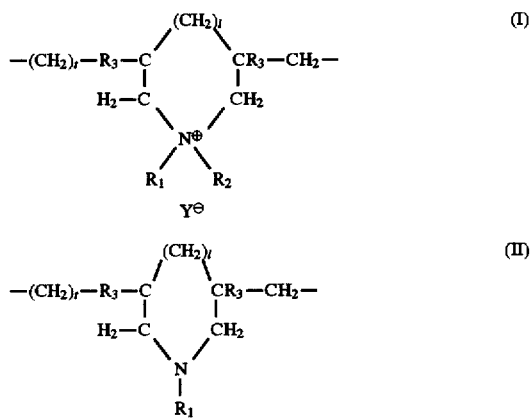

l and t are equal to 0 or 1, and the sum l+t=1;

$R_3$ denotes hydrogen or methyl;

$R_1$ and $R_2$ denote, independently of one another, an alkyl group having from 1 to 22 carbon atoms, a hydroxyalkyl group in which the alkyl group preferably has 1 to 5 carbon atoms, a lower amidoalkyl group and where $R_1$ and $R_2$ can denote, together with the nitrogen atom to which they are attached, heterocyclic groups such as piperidyl or morpholinyl;

$Y^-$ is an anion such as bromide, chloride, acetate, borate, citrate, tartrate, bisulphate, bisulphite, sulphate or phosphate.

Among the polymers defined above, the dimethyldiallylammonium chloride homopolymer sold under the name "MERQUAT 100" by the company MERCK having a molecular weight below 100,000, may be mentioned more especially.

These polymers are described more especially in French Patent 2,080,759 and its Certificate of Addition No. 2,190, 406, the disclosures of which are hereby incorporated by reference.

(6) The poly(quaternary ammonium) polymer containing recurring units corresponding to the formula:

in which $R_4$ and $R_5$, $R_6$ and $R_7$, being identical or different, represent aliphatic, alicyclic or arylaliphatic radicals containing from 1 to 20 carbon atoms or lower hydroxyalkylaliphatic radicals, or alternatively $R_4$ and $R_5$ and $R_6$ and $R_7$, together or separately, constitute, with the nitrogen atoms to which they are attached, heterocycles optionally containing a second hetero atom other than nitrogen, or alternatively $R_4$, $R_5$, $R_6$ and $R_7$ represent a linear or branched $C_1$-$C_6$ alkyl radical substituted with a nitrile, ester, acyl or amide group or a group

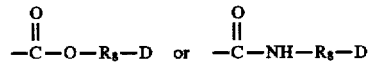

where $R_8$ is an alkylene and D a quaternary ammonium group. $A_1$ and $B_1$ represent polymethylene groups containing from 2 to 20 carbon atoms, which can be linear or branched and saturated or unsaturated and which can contain, linked to or inserted in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from an inorganic or organic acid.

$A_1$ and $R_4$ and $R_6$ can form, with the two nitrogen atoms to which they are attached, a piperazine ring; in addition, if $A_1$ denotes a saturated or unsaturated, linear or branched alkylene or hydroxyalkylene radical, B1 can also denote a group $$(CH_2)_n-CO-D-OC-(CH_2)_n-$$

in which D denotes:

(a) a glycol residue of formula: $-O-Z-O-$ where Z denotes a linear or branched hydrocarbon radical or a group corresponding to the formulae:

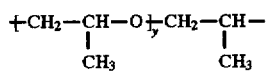

where x and y denote an integer from 1 to 4 representing a defined and unique degree of polymerization, or any number from 1 to 4 representing an average degree of polymerization;

(b) a bis(secondary diamine) residue such as a piperazine derivative;

(c) a bis(primary diamine) residue of formula:

$-NH-Y-NH-$ where Y denotes a linear or branched hydrocarbon radical or alternatively the bivalent radical $-CH_2-CH_2-S-S-CH_2-CH_2-$; and (d) a ureylene group of formula:

$-NH-CO-NH-$ $X^-$ in Formula III is an anion such as chloride or bromide.

These polymers have a molecular mass generally from 1,000 to 100,000.

Polymers of this type are described in particular in French Patents FR 2,320,330, FR 2,270,846, FR 2,316,271, FR 2,336,434 and FR 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of all of which are hereby incorporated by reference.

(7) Poly(quaternary ammonium) polymers comprising units of formula (IV):

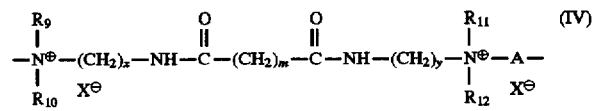

in which:

$R_9$, $R_{10}$, $R_{11}$ and $R_{12}$, which may be identical or different, represent a hydrogen atom or a methyl, ethyl, propyl, β-hydroxyethyl or β-hydroxypropyl radical or a radical $-CH_2CH_2(OCH_2CH_2)_pOH$, where p is equal to 0 or an integer from 1 to 6, with the proviso that $R_9$, $R_{10}$, $R_{11}$ and $R_{12}$ do not simultaneously represent a hydrogen atom;

x and y, which may be identical or different, are integers from 1 to 6;

m is equal to 0 or to an integer from 1 to 34;

X denotes a halogen atom;

A denotes a radical of a dihalide, and preferably represents the residue:

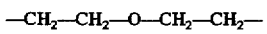

Such compounds are described in greater detail in Application EP-A-122,324, the disclosure of which is hereby incorporated by reference.

Among these, there may be mentioned, for example, the products "MIRAPOL A 15", "MIRAPOL AD1", "MIRAPOL AZI" and "MIRAPOL 175" sold by the company MIRANOL.

The ceramides and/or glycoceramides are known per se, and are natural or synthetic molecules corresponding to the general formula:

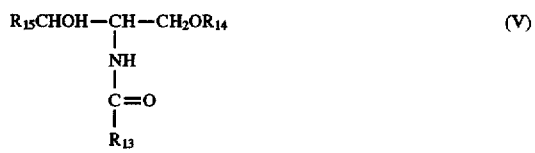

in which:

$R_{13}$ denotes a saturated or unsaturated, linear or branched alkyl radical derived from $C_{14}$–$C_{30}$ fatty acids, it being possible for this radical to be substituted with a hydroxyl group at the α-position or a hydroxyl group at the ω-position esterified with a saturated or unsaturated $C_{16}$–$C_{30}$ fatty acid;

$R_{14}$ denotes a hydrogen atom or a (glycosyl)$_n$, (galactosyl)$_m$ or sulphogalactosyl radical;

in which:

n is an integer varying from 1 to 4; and m is an integer varying from 1 to 8;

$R_{15}$ denotes a $C_{15}$–$C_{26}$ hydrocarbon radical, saturated or unsaturated at the α-position and which can be substituted with one or more $C_1$–$C_{14}$ alkyl radicals; in the case of natural ceramides or glycoceramides, $R_{15}$ can also denote a $C_{15}$–$C_{26}$ α-hydroxyalkyl radical, the hydroxyl group being optionally esterified with a $C_{16}$–$C_{30}$ α-hydroxy acid.

Preferred ceramides are those described by Downing in Arch. Dermatol, Vol. 123, 1381–1384, 1987, or those described in French Patent FR-2,673,179, the disclosure of which is hereby incorporated by reference, the structures of which can be the following:

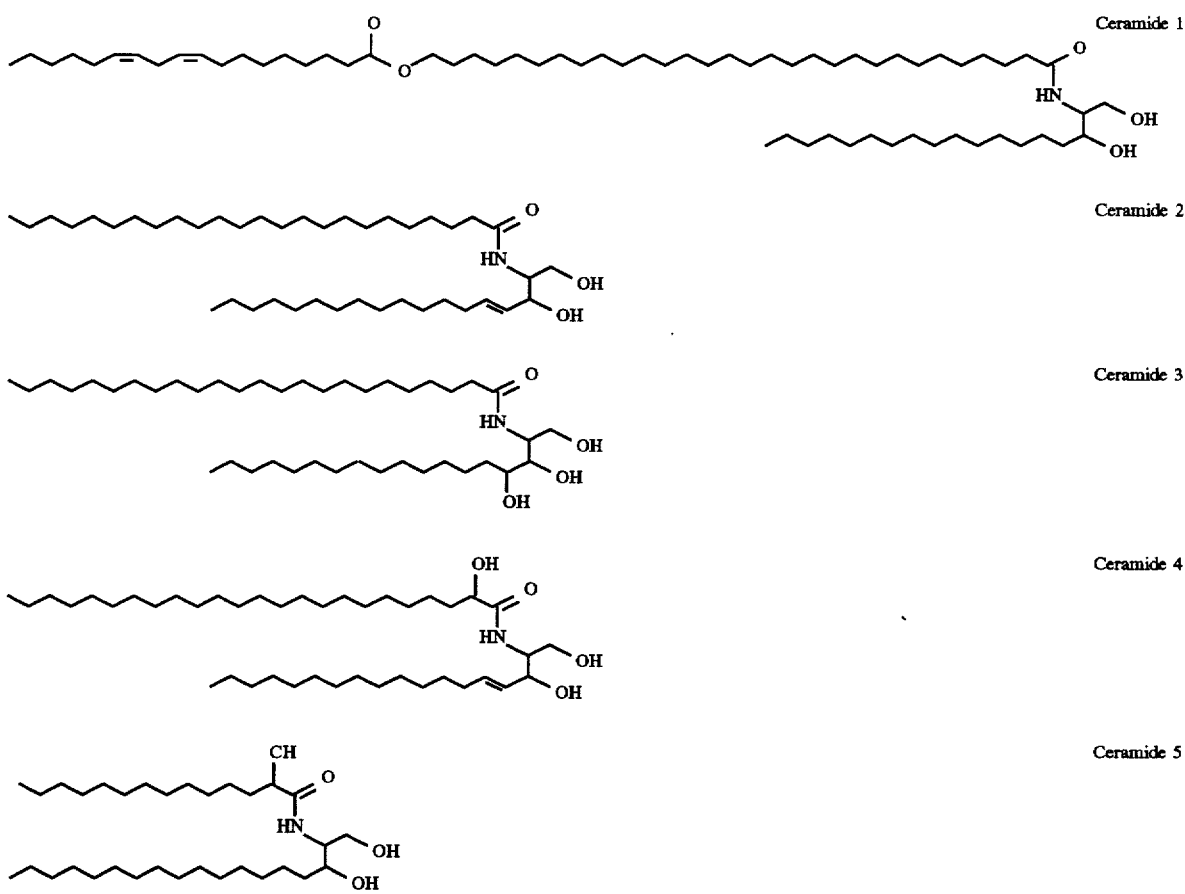

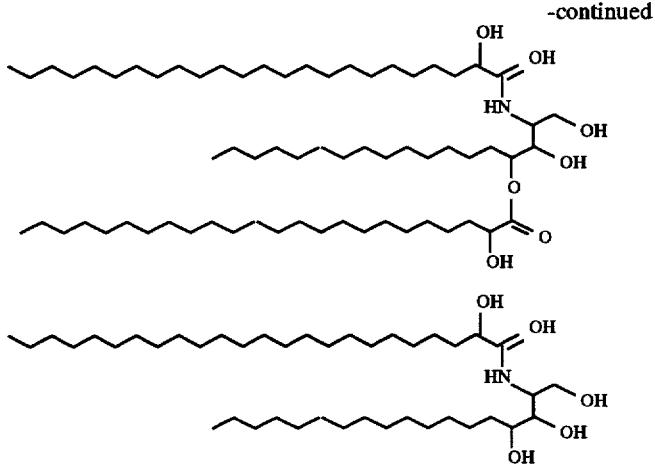

Ceramide 61

Ceramide 611

More especially preferred, ceramides are the compounds of formula (V) for which:

$R_{13}$ denotes a saturated or unsaturated alkyl derived from a $C_{16}$–$C_{22}$ fatty acid;
$R_{14}$ denotes hydrogen;
$R_{15}$ denotes a saturated linear $C_{15}$ radical.

Such compounds are, for example:
- N-linoleoyldihydrosphingosine,
- N-oleoyldihydrosphingosine,
- N-palmitoyldihydrosphingosine,
- N-stearoyldihydrosphingosine,
- N-behenoyldihydrosphingosine,
or mixtures of these compounds.

It is also preferable to use those for which:
$R_{13}$ denotes a saturated or unsaturated alkyl radical derived from a fatty acid;
$R_{14}$ denotes galactosyl or sulphogalactosyl; and
$R_{15}$ denotes —CH==CH—(CH$_2$)$_{12}$—CH$_3$.

The product consisting of a mixture of these compounds, sold under the trade name GLYCOCER by the company WAITAKI INTERNATIONAL BIOSCIENCES may be mentioned.

The cationic polymers are preferably used in proportions of 0.05 to 5% by weight expressed as active substance, and preferably from 0.1 to 3% by weight, relative to the total weight of the composition.

The ceramides and/or glycoceramides are preferably used in proportions of 0.005% to 5% by weight expressed as active substance, and preferably from 0.01 to 3% by weight, relative to the total weight of the composition.

These compositions can contain surfactants, such as non-ionic or cationic surfactants, in proportions generally from 0.1 to 10% by weight.

Nonionic surfactants used in a preferred embodiment of the invention are known per se, and may be chosen from polyethoxyiated, polypropoxylated or polyglycerolated alcohols, alpha-diols, alkylphenols and fatty acids having a fatty chain containing 8 to 18 carbon atoms, it being possible for the number of ethylene oxide and propylene oxide groups to range especially from 2 to 50 and for the number of glycerol groups to range, in particular, from 2 to 30.

There may also be mentioned copolymers of ethylene oxide and propylene oxide, condensates of ethylene oxide and propylene oxide with fatty alcohols; polyethoxylated fatty amides preferably having 2 to 30 mol of ethylene oxide, polyglycerolated fatty amides containing on average 1 to 5 glycerol groups, and especially 1.5 to 4 glycerol groups; polyethoxylated fatty amines preferably having 2 to 3 mol of ethylene oxide; oxyethylenated fatty acid esters of sorbitan having from 2 to 30 mol of ethylene oxide, fatty acid esters of sucrose, fatty acid esters of polyethylene glycol, alkylpolyglycosides, N-alkylglucamine derivatives and amine oxides such as ($C_{10}$–$C_{14}$ alkyl)amine oxides or N-acylaminopropylmorpholine oxides. Alkylpolyglycosides and polyglycerolated alcohols, alpha-diols, alkylphenols and fatty acids are more especially preferred.

The compositions according to the invention can contain cationic surfactants, such as primary, secondary or tertiary fatty amine salts, optionally polyoxyethylenated; quaternary ammonium salts such as tetraalkylammonium, alkylamidoalkyltrialkylammonium, trialkylbenzylarimonium, trialkylhydroxyalkylammonium or alkylpyridinium chlorides or bromides; or imidazoline derivatives.

The compositions can contain thickening agents such as sodium alginate, gum arabic, cellulose derivatives such as methylcellulose, hydroxymethylcellulose, hydroxyethylcellulose hydroxypropylcellulose or hydroxypropylmethylcellulose, guar gum or its derivatives, xanthan gums, scleroglucans, crosslinked polyacrylic acids, polyurethanes or copolymers based on optionally crosslinked maleic acid or anhydride, associative thickeners bearing fatty chains of the natural type, such as the product marketed under the name NATROSOL PLUS, or synthetic thickeners such as the products marketed under the name PEMULEN.

Thickening may also be obtained by mixing polyethylene glycol and polyethylene glycol stearates or distearates, or by mixing amides and phosphoric esters. The cosmetically acceptable medium preferable comprises water or a mixture of water and cosmetically acceptable solvents such as monohydric alcohols, polyhydric alcohols, glycol ethers or fatty acid esters, used alone or mixed. Lower alcohols such as ethanol or isopropanol, polyhydric alcohols such as glycerol or diethylene glycol, glycol ethers and glycol or diethylene glycol alkyl ethers may be mentioned more especially.

The pH of these compositions is generally from 2 to 9, and preferably from 3 to 8. It is adjusted with cosmetically acceptable alkalinizing or acidifying agents which are known per se.

The compositions according to the invention can contain preservatives, sequestering agents, emollients, foam modifiers, acidifying or alcalinizing agents, perfumes, colorants, viscosity modifiers, pearlescent agents, hydrating agents, antidandruff agents, antiseborrhoeic agents, sunscreen agents, proteins, vitamins, hydroxy acids, salts, detoxifying agents, permanent-waving reducing or fixing agents or mixtures thereof.

Other conditioning agents may be used in addition. In this connection, there may be mentioned natural, hydrogenated or unhydrogenated, synthetic or non-synthetic hydrocarbon oils which are cyclic or aliphatic, linear or branched, saturated or unsaturated and soluble or insoluble, fatty alcohols; volatile or non-volatile silicones, organomodified or otherwise and soluble or insoluble in the medium; perfluorinated or fluorinated oils, polybutenes and polyisobutenes, fatty esters occurring in liquid, pasty or solid form, esters of polyhydric alcohols, glycerides, natural or synthetic waxes, silicone gums and resins; proteins; or a mixture of these different agents.

The compositions according to the invention may be used before or after shampooing, before or after permanent-waving or between the reducing and fixing stages, and before or after bleaching or dyeing or straightening. They may also be used for the dyeing of keratinous fibers such as hair, in which case they contain oxidation dyes and/or direct dyes which are well known in the hair dyeing field. Dyes of this type are described, in particular, in Charles ZVIAK "Sciences des Traitements capillaires" [Hair treatment science] Ed. Masson, 1988, the disclosure of which is hereby incorporated by reference. These compositions may also be used for permanent-waving in which case they contain reducing agents or fixing or neutralizing agents, depending on whether the composition is used for reducing or fixing hair. Such products are described, in particular, in Charles ZVIAK "Sciences des Traitements capillaires" mentioned above.

These products generally take the form of emulsions or dispersions or solutions. They can also be in the form of fluid or thickened liquids, gels or creams. They may be used as they are or be diluted before use. They can also be packaged in a container under pressure and be delivered in spray, liquid, cream, gel or foam form. They may be rinsed or non-rinsed.

Another subject of the invention is drawn to a process for the treatment of hair, comprising applying a composition as defined above to the hair to be treated and in optionally carrying out rinsing.

The examples which follow are intended to illustrate the invention, no limitation of the latter being, however, implied.

EXAMPLES

Example 1

The following composition was prepared:

| | | |
|---|---|---|
| Polyquaternium 2 (CTFA), sold under the name MIRAPOL A 15 | 1 g | AS |
| Ceramide A | 0.5 g | |
| APG 300, which is a (C$_9$/C$_{10}$/C$_{11}$ alkyl) polyglycoside (1, 4), sold in aqueous solution containing 50% of active substance (AS) by the company HENKEL | 2 g | |
| Hydroxyethylcellulose | 0.5 g | |
| Water | qs | 100 9 |
| pH adjusted to 7.5 with NaOH | | |

Pressurization scheme: 90 g of composition
10 g Aérogaz 3–2

This composition formed a foam at the outlet of the aerosol device, which foam was applied to the hair and disappeared after being massaging in.

Ceramide A:
N-oleoyldihydrosphingosine of formula:

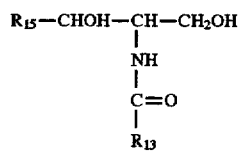

in which:
$R_{15}=C_{15}H_{31}$
$R_{15}=C_{17}H_{33}$

Polymer A:
Polymer containing units of formula:

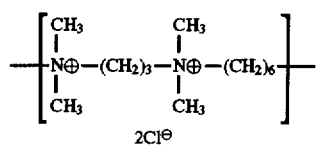

prepared and described in French Patent No. 2,270,846.

Examples 2 to 5

| EXAMPLE | 2 | 2A | 2B |
|---|---|---|---|
| Ceramide A | 0.2 g | 0.7 g | — |
| Polymer A | 0.5 g | — | 0.7 g |
| 2-Propanol | 60 g | 60 g | 60 g |
| Water qs | 100 g | 100 g | 100 g |

Examples 2A and 2B were not prepared according to the invention, but were comparative examples.

5 g of the compositions were applied to previously washed and rinsed locks weighing 2.5 g. The compositions were left in place for 5 minutes and the hair was then rinsed in running water. The disentangling of the wet hair was then evaluated.

It was found that the disentangling for the composition 2 was markedly superior to the disentangling obtained with the compositions 2A and 2B containing only either the ceramide or the cationic polymer.

Similar results were obtained using the following polymers in place of the polymer A: MIRAPOL A 15, MERQUAT 100, and a polycondensate of diethylenediamine and adipic acid crosslinked with epichlorohydrin, described in French Patent FR-2,252,840.

MERQUAT 100 (CALGON)=dimethyldiallylammonium chloride homopolymer (polyquaternium-6).

Example 6

The following composition was prepared:

| | |
|---|---|
| 1-Amino-4-(β-3-methoxyethylamino)benzene dihydrochloride | 0.71 g |
| 1-Hydroxyethyloxy-2,4-diaminobenzene dihydrochloride | 0.72 g |
| Cetyl and stearyl alcohols in 50:50 mixture | 18 g |
| 2 Octyldodecanol | 3 g |
| Oxyethylenated cetyl/stearyl alcohol containing 15 mol of ethylene oxide | 3 g |

| | |
|---|---|
| Ammonium laurel sulphate containing 30% of AS (3.6 g AS) | 12 g |
| N-Oleoyldihydrosphingosine | 0.3 g |
| Polymer consisting of units of formula: | 3 g |

$$\left[ \begin{array}{cc} \underset{|}{\overset{CH_3}{|}} & \underset{|}{\overset{CH_3}{|}} \\ -N^{\oplus}-(CH_2)_3-N^{\oplus}-(CH_2)_6- \\ \underset{}{\overset{CH_3}{}} & \underset{}{\overset{CH_3}{}} \\ & 2\,Cl^{\ominus} \end{array} \right]$$

| | |
|---|---|
| which was be prepared as described in French Patents FR 2,270,846 and 2,333,012. | |
| Ammonia solution, 22° Bé | 12 g |
| Sodium bisulphite, 35° Bé | 1.5 g |
| Perfume | qs |
| Demineralized water | qs 100 g |

This dyeing composition was a cream, which was mixed with 1.5 times its weight of 20-volumes hydrogen peroxide. The creamy mixture obtained was applied for 30 minutes to 90%-white grey hair.

After rinsing and shampooing, a blue hue was obtained.

Example 7

The following reducing composition was prepared:

| | |
|---|---|
| Thiolactic acid | 8 g |
| Ammonia solution qs pH7 | |
| Ammonium bicarbonate | 6.5 g |
| Sequestering agent | 0.2 g |
| N-Oleoyldihydrosphingosine | 0.1 g |
| Polymer consisting of units of formula | 3 g |

$$\left[ \begin{array}{cc} \underset{|}{\overset{CH_3}{|}} & \underset{|}{\overset{CH_3}{|}} \\ -N^{\oplus}-(CH_2)_3-N^{\oplus}-(CH_2)_6- \\ \underset{}{\overset{CH_3}{}} & \underset{}{\overset{CH_3}{}} \\ & 2\,Cl^{\ominus} \end{array} \right]$$

| | |
|---|---|
| which can be prepared as described in French Patents 2,270,846 and 2,333,012. | |
| $C_9/C_{10}/C_{11}$ alkyl polyglycoside (1,4) (APG 300) | 3.5 g AS |
| Perfume | qs |
| Demineralized water | qs 100 g |

The hair was wound on rollers varying from 4 mm to 10 mm in diameter, and the composition was then left to act for an exposure time of 10 to 15 minutes.

After rinsing, an oxidizing composition based on 8-volumes hydrogen peroxide and having a pH of 4 was then applied to the reduced hair.

This oxidizing composition was left to act for 5 minutes, thereafter the hair was rinsed and the rollers then removed. The hair then had attractive curls.

What is claimed is:

1. A composition for the treatment and protection of hair, comprising, in a cosmetically acceptable medium:
   at least one ceramide and/or glycoceramide and
   at least one cationic polymer containing primary, secondary or tertiary amine groups or quaternary ammonium groups in the main chain, said at least one cationic polymer having a viscosity at a concentration of 1% by weight of active substance in water of less than 15 mPa.s; and
   from 0 to less than 4 % by weight of at least one surfactant selected from anionic, amphoteric, and zwitterionic surfactants.

2. A composition according to claim 1, wherein said at least one cationic polymer is:
   (1) a polymer comprising piperazinyl units and bivalent alkylene or hydroxyalkylene radicals having unbranched or branched chains, optionally interrupted by oxygen, sulphur or nitrogen atoms or by aromatic or heterocyclic rings, or the oxidation and/or quaternization products of said polymer;
   (2) a water-soluble polyaminoamide, optionally cross-linked and/or alkylated;
   (3) a polyaminoamide compound resulting from the condensation of a polyalkylenepolyamine with a polycarboxylic acid, followed by an alkylation with a bifunctional agent;
   (4) a polymer obtained by reacting a polyalkylenepolyamine containing two primary amine groups and at least one secondary amine group with a dicarboxylic acid;
   (5) a methyldiallylamine or dimethyldiallylammonium cyclohomopolymer; or
   (6) a poly(quaternary ammonium)polymer.

3. A composition according to claim 1, wherein said at least one ceramide and/or glycoceramide is a compound of formula:

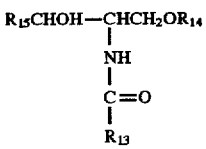

in which:

$R_{13}$ denotes a saturated or unsaturated, linear or branched alkyl radical derived from $C_{14}$-$C_{30}$ fatty acids, said radical optionally being substituted with a hydroxyl group at the α-position, wherein the hydroxyl group is esterified with a saturated or unsaturated $C_{16}$-$C_{30}$ fatty acid, or a hydroxyl group at the ω-position, wherein the hydroxyl group is esterified with a saturated or unsaturated $C_{16}$-$C_{30}$ fatty acid;
$R_{14}$ denotes a hydrogen atom or a (glycosyl)$_n$, (galactosyl)$_m$ or sulphogalactosyl radical;

where n is an integer varying from 1 to 4; and m is an integer varying from 1 to 8; and $R_{15}$ denotes a $C_{15}$-$C_{26}$ hydrocarbon radical, saturated or unsaturated at the α-position, optionally substituted with one or more $C_1$-$C_{14}$ alkyl radicals;

wherein in the case of natural ceramides or glycoceramides, $R_{15}$ may also denote a $C_{15}$-$C_{26}$ α-hydroxyalkyl radical, the hydroxyl group being optionally esterified with a $C_{16}$-$C_{30}$ α-hydroxy acid.

4. A composition according to claim 1, wherein said at least one cationic polymer is present in proportions ranging from 0.05 to 5% by weight expressed as active substance relative to the total weight of the composition.

5. A composition according to claim 4, wherein said at least one cationic polymer is present in proportions ranging from 0.1 to 3% by weight expressed as active substance relative to the total weight of the composition.

6. A composition according to claim 1, wherein said at least one ceramide and/or glycoceramide is present in proportions ranging from 0.005 to 5% by weight expressed as active substance relative to the total weight of the composition.

7. A composition according to claim 6, wherein said at least one ceramide and/or glycoceramide is present in proportions ranging from 0.01 to 3% by weight expressed as active substance relative to the total weight of the composition.

8. A composition according to claim 1, wherein the pH of the composition ranges from 2 to 9.

9. A composition according to claim 1, wherein said composition further comprises at least one surfactant selected from nonionic and cationic surfactants.

10. A composition according to claim 1, wherein said composition further comprises thickening agents.

11. A composition according to claim 1, wherein said cosmetically acceptable medium comprises water or a mixture of water and cosmetically acceptable solvents, wherein said solvents are monohydric alcohols, polyhydric alcohols, glycol ethers or fatty acid esters, used alone or mixed.

12. A composition according to claim 1, wherein said composition further comprises preservatives, sequestering agents, emollients, foam modifiers, colorants, viscosity modifiers, pearlescent agents, hydrating agents, antidandruff agents, antiseborrhoeic agents, sunscreen agents, proteins, vitamins, α-hydroxy acids, salts, detoxifying agents, perfumes, permanent-waving reducing or fixing agents or mixtures thereof.

13. A composition according to claim 1, wherein said composition further comprises other conditioning agents, wherein said other conditioning agents are natural, hydrogenated or unhydrogenated, synthetic or non-synthetic oils which are cyclic or aliphatic, linear or branched and saturated or unsaturated, fatty alcohols; volatile or non-volatile silicones, which are organomodified and which are soluble or insoluble in the medium; fluorinated or perfluorinated oils; polybutenes, polyisobutenes; fatty esters, esters of polyhydric alcohols; glycerides; synthetic or natural waxes, silicone gums and resins; proteins; or mixtures thereof.

14. A composition according to claim 1, wherein said composition is in the form of a fluid, a thickened liquid, a gel, a cream, or a foam, optionally packaged under pressure.

15. A non-washing process for the treatment and protection of hair, comprising the steps of applying to the hair a composition as defined in claim 1, and, after an optional period of exposure, optionally rinsing the hair.

16. A process for the non-washing treatment of hair comprising the step of applying to the hair a composition as defined in claim 1.

17. A process for the dyeing of hair comprising the step of applying to the hair a composition according to claim 1.

18. A process for the permanent-waving of hair comprising the step of applying to the hair a composition according to claim 1.

* * * * *